(12) United States Patent
Aoki

(10) Patent No.: US 8,236,155 B2
(45) Date of Patent: Aug. 7, 2012

(54) EXHAUST GAS SENSOR

(75) Inventor: Keiichiro Aoki, Numazu (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 196 days.

(21) Appl. No.: 12/673,978

(22) PCT Filed: Dec. 19, 2008

(86) PCT No.: PCT/JP2008/073891
§ 371 (c)(1),
(2), (4) Date: Feb. 18, 2010

(87) PCT Pub. No.: WO2009/098833
PCT Pub. Date: Aug. 13, 2009

(65) Prior Publication Data
US 2011/0067481 A1 Mar. 24, 2011

(30) Foreign Application Priority Data
Feb. 4, 2008 (JP) ................................. 2008-024136

(51) Int. Cl.
*G01N 27/407* (2006.01)
(52) U.S. Cl. ....................................... 204/429; 204/427
(58) Field of Classification Search .................. 204/424, 204/427, 429; 205/784.5
See application file for complete search history.

(56) References Cited

U.S. PATENT DOCUMENTS

| | | | | |
|---|---|---|---|---|
| 4,101,403 A | * | 7/1978 | Kita et al. | 204/410 |
| 5,302,276 A | * | 4/1994 | Kato et al. | 204/429 |
| 2002/0063059 A1 | * | 5/2002 | Sugiyama et al. | 204/426 |
| 2007/0170057 A1 | | 7/2007 | Kobayashi et al. | |

FOREIGN PATENT DOCUMENTS

| | | |
|---|---|---|
| CN | 101008630 A | 8/2007 |
| DE | 10 2004 054 014 | 5/2006 |
| EP | 1 742 043 | 1/2007 |
| JP | 2002 633 | 2/2002 |
| JP | 2003 322632 | 11/2003 |

(Continued)

OTHER PUBLICATIONS

Office Action issued Aug. 9, 2011 in Japan Application No. 2008-024136.

(Continued)

*Primary Examiner* — Kaj K Olsen
(74) *Attorney, Agent, or Firm* — Oblon, Spivak, McClelland, Maier & Neustadt, L.L.P.

(57) ABSTRACT

An exhaust gas sensor that simultaneously exhibits enhanced water soak resistance and functionality, that is multilayered and exposed to a space in an exhaust path. The exhaust gas sensor includes: an electrolyte layer, positioned between an exhaust electrode and an atmosphere electrode; an atmospheric layer formation layer formed toward the atmosphere electrode to form an atmospheric layer to which the atmosphere electrode is exposed; a porous diffusion resistance layer formed toward the exhaust electrode to control flow rate of an exhaust gas reaching the exhaust electrode; and a porous trap layer formed to cover the entire section exposed to the space in the exhaust path. The trap layer includes a first trap layer, which covers a region near a gas inlet/outlet section of the diffusion resistance layer, and a second trap layer, which covers another region that covered by the first trap layer. The first trap layer is thinner than the second trap layer.

5 Claims, 2 Drawing Sheets

FOREIGN PATENT DOCUMENTS

| | | |
|---|---|---|
| JP | 2005-195516 | 7/2005 |
| JP | 2005-300471 | 10/2005 |
| JP | 2006-242667 | 9/2006 |
| JP | 2007-139749 | 6/2007 |
| JP | 2007 206082 | 8/2007 |
| JP | 2009-80099 | 4/2009 |
| WO | 2008 151054 | 12/2008 |

OTHER PUBLICATIONS

Office Action issued Nov. 29, 2011, in Japanese Patent Application No. 2008-024136.

Chinese Office Action issued Apr. 16, 2012 in corresponding Chinese Application No. 2008801034205 (not translated).

* cited by examiner

EXHAUST GAS SENSOR

CROSS-REFERENCES TO RELATED APPLICATIONS

This application is a National Stage entry of PCT/JP2008/073891 which itself claims priority to JP 2008-024136.

TECHNICAL FIELD

The present invention relates to an exhaust gas sensor, and more particularly to the structure of an exhaust gas sensor.

BACKGROUND ART

A conventional multilayered gas sensor disclosed, for instance, in JP-A-2003-322632 prevents its sensor element from cracking even when water droplets are attached to it. At least, a porous protective layer composed of a porous adhesion layer and a porous surface layer is formed over the entire circumferential surface of the gas sensor's leading end, which is to be exposed to the gas to be measured. The porous protective layer is formed in such a manner that its thickness is at least 20 μm as measured from the element's four longitudinally extended corners. Therefore, even when water droplets are attached to a crack-prone corner of the element, the water droplets disperse within the porous protective layer, thereby effectively preventing the element from cracking.

Patent Document 1:
JP-A-2003-322632
Patent Document 2:
JP-A-2007-206082
Non-patent Document 1:
JIII Journal of Technical Disclosure No. 2002-633

DISCLOSURE OF INVENTION

Problem to be Solved by the Invention

As is the case with the above-mentioned conventional gas sensor, the water soak resistance of an exhaust gas sensor increases with an increase in the thickness of a porous layer covering the entire circumferential surface of an exhaust gas sensor's sensor element that is exposed to exhaust gas. However, such an increase in the thickness of the porous layer unduly restricts the speed of an exhaust gas reaching an exhaust gas side electrode. This impairs the output response of the sensor. Further, exhaust gas components attach to the porous layer during a period of engine inactivity. When the attached exhaust gas components become detached during engine warm-up for a cold start, the exhaust gas components change in the vicinity of the electrode. This causes the output of the sensor to deviates from normal. The thicker the porous layer becomes, the larger the amount of exhaust gas components attaches to. Therefore, an increase in the thickness of the porous layer increases the period during which the sensor output deviates from normal, thereby affecting the air-fuel ratio control performance of a system.

The present invention has been made to solve the above problem. It is an object of the present invention to provide an exhaust gas sensor that simultaneously exhibits enhanced water soak resistance and functionality.

Means for Solving the Problem

First aspect of the present invention is an exhaust gas sensor that is multilayered and exposed to a space in an exhaust path of an internal combustion engine, the exhaust gas sensor comprising:

an electrolyte layer which is positioned between an exhaust electrode and an atmosphere electrode to permit the movement of oxygen ions between the electrodes;

an atmospheric layer formation layer which is placed on the atmosphere electrode side of the electrolyte layer to form an atmospheric layer to which the atmosphere electrode is exposed;

a diffusion resistance layer which is porous and placed on the exhaust electrode side of the electrolyte layer to control the flow rate of an exhaust gas reaching the exhaust electrode; and a trap layer which is porous and formed to cover the entire section exposed to the space in the exhaust path;

wherein the trap layer includes a first trap layer, which covers a region near a gas inlet/outlet section of the diffusion resistance layer, and a second trap layer, which covers the other region that is not covered by the first trap layer, the first trap layer being thinner than the second trap layer.

Second aspect of the present invention is the exhaust gas sensor according to the first aspect, further comprising:

a heater layer in which a heater is embedded to heat the electrolyte layer;

wherein the second trap layer is formed to cover a region near the heater layer.

Third aspect of the present invention is an exhaust gas sensor that is multilayered and exposed to a space in an exhaust path of an internal combustion engine, the exhaust gas sensor comprising:

an electrolyte layer which is positioned between an exhaust electrode and an atmosphere electrode to permit the movement of oxygen ions between the electrodes;

an atmospheric layer formation layer which is placed on the atmosphere electrode side of the electrolyte layer to form an atmospheric layer to which the atmosphere electrode is exposed;

a diffusion resistance layer which is porous and placed on the exhaust electrode side of the electrolyte layer to control the flow rate of an exhaust gas reaching the exhaust electrode; and a trap layer which is porous and formed to cover the entire section exposed to the space in the exhaust path;

wherein the trap layer includes a first trap layer, which covers a region near a gas inlet/outlet section of the diffusion resistance layer, and a second trap layer, which covers the other region that is not covered by the first trap layer, the first trap layer being higher in porosity than the second trap layer.

Fourth aspect of the present invention is the exhaust gas sensor according to the third aspect, further comprising:

a heater layer in which a heater is embedded to heat the electrolyte layer;

wherein the second trap layer is formed to cover a region near the heater layer.

Fifth aspect of the present invention is the exhaust gas sensor according to the third or the fourth aspects, wherein the first trap layer is equal in thickness to the second trap layer.

Sixth aspect of the present invention is an exhaust gas sensor that is multilayered and exposed to a space in an exhaust path of an internal combustion engine, the exhaust gas sensor comprising:

an electrolyte layer which is positioned between an exhaust electrode and an atmosphere electrode to permit the movement of oxygen ions between the electrodes;

an atmospheric layer formation layer which is placed on the atmosphere electrode side of the electrolyte layer to form an atmospheric layer to which the atmosphere electrode is exposed;

a diffusion resistance layer which is porous and placed on the exhaust electrode side of the electrolyte layer to control the flow rate of an exhaust gas reaching the exhaust electrode; and a trap layer which is porous and formed to cover the section exposed to the space in the exhaust path;

wherein the trap layer is formed to cover a region except the vicinity of a gas inlet/outlet section of the diffusion resistance layer.

Seventh aspect of the present invention is the exhaust gas sensor according to the sixth aspect, further comprising:

a heater layer in which a heater is embedded to heat the electrolyte layer;

wherein the trap layer is formed to cover a region near the heater layer.

Advantages of the Invention

In the multilayered exhaust gas sensor, the porous trap layer is formed to cover the entire surface of the exposed portion in the exhaust path of the internal combustion engine. When the exhaust gas sensor is covered with the trap layer, it is possible to effectively reduce thermal shock that is undergone when the sensor is soaked in water in the exhaust gas. Therefore, the generation of a crack or the like can be effectively suppressed. Meanwhile, the trap layer adsorbs exhaust gas components in the exhaust path during a period of engine inactivity, and desorbs the adsorbed components during a warm-up period. Therefore, when a thick trap layer is provided near the gas inlet/outlet section of the diffusion resistance layer, the desorbed adsorbed components are introduced in large amounts into the diffusion resistance layer. This causes the output of the sensor to deviate from normal for a long period of time. According to the first aspect of the present invention, the first trap layer, which covers the vicinity of the gas inlet/outlet section of the diffusion resistance layer, is thinner than the second trap layer, which covers the other portion. Consequently, the present invention effectively reduces the amounts of the desorbed exhaust gas components introduced into the diffusion resistance layer, thereby shortening the period during which the sensor output deviates from normal. This makes it possible to simultaneously improve the sensor's water soak resistance and functionality.

According to the second aspect of the present invention, the exhaust gas sensor includes the heater layer in which a heater is embedded to heat the electrolyte layer. Further, the second trap layer, which is thicker than the first trap layer, is formed to cover the vicinity of the heater layer. The heater layer is likely to crack due to thermal shock caused by water soaking because it is higher in temperature than the other sections. Therefore, the present invention effectively improves the water soak resistance in the vicinity of the heater layer.

In the multilayered exhaust gas sensor, the porous trap layer is formed to cover the entire surface of the exposed portion in the exhaust path of the internal combustion engine. The lower the porosity of the porous trap layer is, the greater the degree to which thermal shock caused by water soaking is reduced. Therefore, when the exhaust gas sensor is covered with a low-porosity trap layer, it is possible to effectively suppress the generation of a crack or the like due to water soaking. Meanwhile, the trap layer adsorbs exhaust gas components in the exhaust path during a period of engine inactivity, and desorbs the adsorbed components during a warm-up period. The higher the porosity of the porous trap layer is, the smaller its surface area is, and thus the smaller the amounts of adsorbable exhaust gas components becomes. Therefore, when a low-porosity trap layer is provided near the gas inlet/outlet section of the diffusion resistance layer, the exhaust gas components are adsorbed in large amounts. This causes the output of the sensor to deviate from normal for a long period of time. According to the third aspect of the present invention, the first trap layer, which covers the vicinity of the gas inlet/outlet section of the diffusion resistance layer, has a higher porosity than the second trap layer, which covers the other portion. Consequently, the present invention not only effectively shortens the period during which the output of the exhaust gas sensor deviates from normal, but also effectively suppresses the generation of a crack or the like due to water soaking.

According to the fourth aspect of the present invention, the exhaust gas sensor includes the heater layer in which a heater is embedded to heat the electrolyte layer. Further, the second trap layer, which has a lower porosity than the first trap layer, is formed to cover the vicinity of the heater layer. The heater layer is likely to crack due to thermal shock caused by water soaking because it is higher in temperature than the other sections. Therefore, the present invention effectively improves the water soak resistance in the vicinity of the heater layer.

According to the fifth aspect of the present invention, the first trap layer is equal in thickness to the second trap layer. Therefore, the present invention effectively enhances the water soak resistance of a region covered by the first trap layer, which has a high porosity.

The trap layer adsorbs exhaust gas components in the exhaust path during a period of engine inactivity, and desorbs the adsorbed components during a warm-up period. Therefore, when a thick trap layer is provided near the gas inlet/outlet section of the diffusion resistance layer, the desorbed adsorbed components are introduced in large amounts into the diffusion resistance layer. This causes the output of the sensor to deviate from normal for a long period of time. Meanwhile, the diffusion resistance layer rarely cracks due to water soaking. It is therefore conceivable that adequate water soak resistance may be obtained without providing protection with the trap layer. According to the sixth aspect of the present invention, the trap layer is formed to cover a region except the vicinity of the gas inlet/outlet section of the diffusion resistance layer. Thus, the present invention does not provide a trap layer for a region near the gas inlet/outlet section of the diffusion resistance layer. Consequently, the amounts of desorbed exhaust gas components introduced into the diffusion resistance layer can be effectively reduced to shorten the period during which the sensor output deviates from normal. This makes it possible to simultaneously improve the sensor's water soak resistance and functionality.

According to the seventh aspect of the present invention, the exhaust gas sensor includes the heater layer in which a heater is embedded to heat the electrolyte layer. Further, the trap layer is formed to cover the vicinity of the heater layer. The heater layer is likely to crack due to thermal shock caused by water soaking because it is higher in temperature than the other sections. Therefore, the present invention effectively improves the water soak resistance in the vicinity of the heater layer.

BEST MODE FOR CARRYING OUT THE INVENTION

Figure 1:
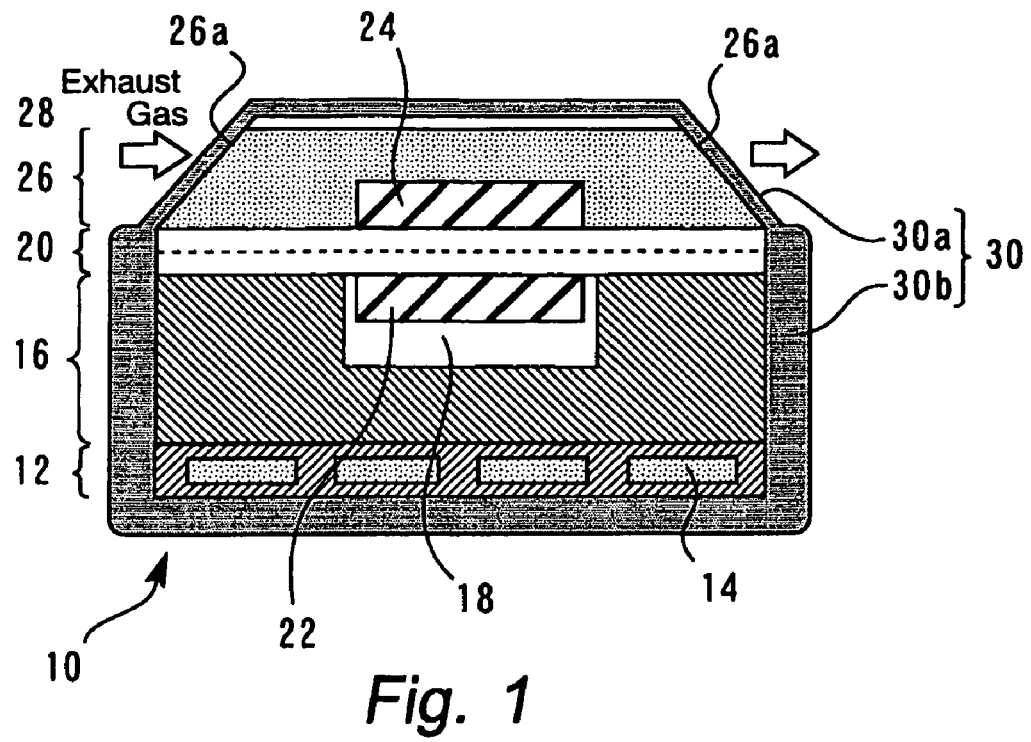
FIG. 1 is a diagram illustrating the configuration of a multilayered air-fuel ratio sensor 10 for use in a first embodiment of the present invention.

Embodiments of the present invention will now be described with reference to the accompanying drawings. Like elements in the drawings are designated by the same reference numerals and will not be redundantly described. It should be understood that the present invention is not limited to the embodiments described below.

First Embodiment

Configuration of Air-Fuel Ratio Sensor

FIG. 1 is a diagram illustrating the configuration of a multilayered air-fuel ratio sensor 10 for use in a first embodiment of the present invention. More specifically, FIG. 1 is a cross-sectional view illustrating a sensor element section of the air-fuel ratio sensor 10. The air-fuel ratio sensor 10 includes a sensor element, which has a cross-sectional structure shown in FIG. 1, and a cover for protecting the sensor element. The air-fuel ratio sensor 10 is installed in an exhaust path of an internal combustion engine so that the covered sensor element is exposed to exhaust gas.

The cover for the air-fuel ratio sensor 10 has a plurality of vent holes so that the gas passing through the inside of the exhaust path reaches the sensor element. Therefore, the air-fuel ratio sensor 10 (sensor element) shown in FIG. 1 is in a state where its circumferential surface is exposed to the exhaust gas.

The air-fuel ratio sensor 10 includes a heater layer 12. A heater 14 is embedded in the heater layer 12 to heat the sensor element to an activation temperature. Referring to FIG. 1, an atmospheric layer formation layer 16 is positioned above the heater layer 12. The atmospheric layer formation layer 16 is made of ceramics such as alumina.

An electrolyte layer 20 made, for instance, of zirconia is positioned above the atmospheric layer formation layer 16. A dent is made in the upper central portion of the atmospheric layer formation layer 16 to form an atmospheric layer 18. The atmospheric layer 18 is isolated from a space in the exhaust path by the atmospheric layer formation layer 16 and the electrolyte layer 20, and open to the atmosphere through an atmospheric hole (not shown).

An atmosphere electrode 22 is exposed to the atmospheric layer 18 by positioning it below the electrolyte layer 20. Meanwhile, an exhaust electrode 24 is positioned above the electrolyte layer 20. The exhaust electrode 24 is covered with a diffusion resistance layer 26. The diffusion resistance layer 26 is a porous substance and capable of properly controlling the flow rate of the gas reaching the exhaust electrode 24 through the exhaust path.

A shield layer 28 is positioned above the diffusion resistance layer 26. The shield layer 28 covers the top of the diffusion resistance layer 26 so that the inlet/outlet for the gas flowing into the diffusion resistance layer 26 is limited to an inlet/outlet section 26a.

The air-fuel ratio sensor 10 according to the present embodiment includes a trap layer 30, which covers the entire circumferential surface of the sensor element exposed to the space in the exhaust path. The trap layer 30 is a porous substance and mainly composed of ceramics such as alumina. Further, the thickness of the trap layer 30, which covers the sensor element, varies from one region to another. More specifically, a thin trap layer 30a is positioned in a region that covers the vicinity of the inlet/outlet section 26a of the diffusion resistance layer 26 for the sensor element. In addition, another trap layer 30b, which is thicker than the above-mentioned trap layer 30a, is positioned in a region that mainly covers the heater layer 12 and the atmospheric layer formation layer 16.

Features of First Embodiment

Features of the present embodiment will now be described. As described earlier, the air-fuel ratio sensor 10 is positioned so that the sensor element is exposed to the space in the exhaust path of the internal combustion engine. The air-fuel ratio sensor 10 delivers its expected performance when it becomes active as the sensor element receives heat from the heater 14 or exhaust heat.

The exhaust gas flowing in the exhaust path contains water droplets and oil droplets. Thus, when a high-temperature sensor element is soaked in water, it may crack due to thermal shock. Consequently, the air-fuel ratio sensor 10 according to the present embodiment uses the trap layer 30 to protect the entire surface of the sensor element exposed to the space in the exhaust path. More specifically, the trap layer 30 is formed to cover the circumferential surface of the sensor element, which is a multilayered structure composed of the heater layer 12, atmospheric layer formation layer 16, electrolyte layer 20, diffusion resistance layer 26, and shield layer 28, as shown in FIG. 1. The trap layer 30 is made of porous ceramic. Therefore, when the trap layer 30 is soaked in the water in the exhaust gas, the water permeates into the porous material and diffuses, thereby reducing the thermal shock applied to the sensor element. This makes it possible to effectively prevent the element of the air-fuel ratio sensor 10 from being cracked by water soaking.

As described above, the trap layer 30 can effectively prevent the element of the air-fuel ratio sensor 10 from being cracked by water soaking. In addition, the thicker the trap layer 30, the greater the degree to which thermal shock caused by water soaking is reduced. However, an increase in the thickness of the trap layer 30 may increase the period during which the sensor output deviates from normal in a warm-up process for the internal combustion engine. More specifically, while the internal combustion engine remains inactive, hydrocarbon (HC) and other rich gas components contained, for instance, in the exhaust gas that fills the exhaust path become adsorbed by the trap layer 30 made of ceramics. The adsorbed rich gas components become desorbed during a warm-up period of the internal combustion engine. This increases the amounts of the rich gas components passing through the diffusion resistance layer 26 and causes the sensor output to deviate from normal. In particular, the amounts of adsorbed rich gas components increase with an increase in the thickness of the trap layer 30, thereby increasing the period during which the sensor output deviates from normal in a warm-up process of the internal combustion engine.

In view of the above circumstances, the air-fuel ratio sensor 10 according to the present embodiment includes the thin trap layer 30a, which is positioned in a region that covers the vicinity of the inlet/outlet section 26a of the diffusion resistance layer 26 for the sensor element. This reduces the amounts of rich gas components that attach to the vicinity of the inlet/outlet section 26a during a period of internal combustion engine inactivity. This makes it possible to effectively avoid a situation where the desorbed rich gas components enter the diffusion resistance layer 26 to increase the period during which the sensor output deviates from normal. In addition, another trap layer 30b, which is thicker than the above-mentioned trap layer 30a, is positioned, for instance, in the vicinity of the heater layer 12 in which the sensor element is likely to crack. This makes it possible to effectively protect the sensor element from thermal shock caused by water soaking.

As described above, the air-fuel ratio sensor 10 according to the present embodiment uses the trap layers 30a, 30b, which differ in thickness, to effectively avoid a situation where sensor output deviation persists for a long period of time and effectively prevent the sensor element from being cracked by water soaking. This makes it possible to simultaneously enhance the air-fuel ratio sensor's functionality and water soak resistance.

The first embodiment, which has been described above, assumes that the air-fuel ratio sensor 10 includes the trap layers 30a, 30b, which differ in thickness, to simultaneously enhance the sensor's functionality and water soak resistance. However, the present invention is applicable not only to air-fuel ratio sensors but also to oxygen sensors and other exhaust gas sensors as far as they are multilayered and exposed to the gas to be measured.

Further, the first embodiment, which has been described above, assumes that the trap layer 30 is made of porous alumina. However, the present invention is not limited to the use of such a trap layer. More specifically, the trap layer 30 may be made of any porous ceramic materials.

Figure 3:
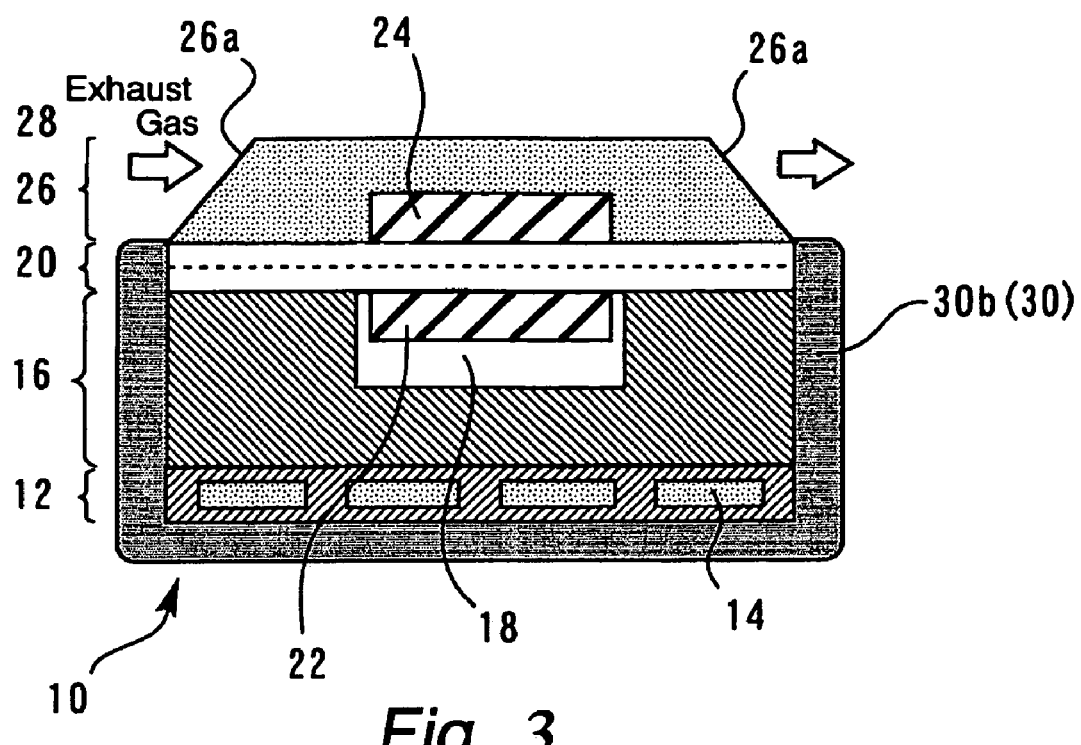
FIG. 3 is a diagram illustrating the configuration of a multilayered air-fuel ratio sensor 10 for use in a first embodiment of the present invention.

Further, the first embodiment, which has been described above, assumes that the thin trap layer 30a is positioned at the inlet/outlet section 26a of the diffusion resistance layer 26. However, the diffusion resistance layer 26 is not likely to crack due to thermal shock. Therefore, as shown in FIG. 3, the trap layer 30a may be eliminated to further improve the sensor's functionality. This makes it possible to effectively shorten the period during which sensor output deviation persists in a warm-up process, thereby further enhancing the sensor's functionality.

In the first embodiment, which has been described above, the air-fuel ratio sensor 10 corresponds to the "exhaust gas sensor" according to the first aspect of the present invention; the trap layer 30a corresponds to the "first trap layer" according to the first aspect of the present invention; and the trap layer 30b corresponds to the "second trap layer" according to the first aspect of the present invention.

Further, in the first embodiment, which has been described above, the air-fuel ratio sensor 10 corresponds to the "exhaust gas sensor" according to the sixth aspect of the present invention; and the trap layer 30b corresponds to the "trap layer" according to the sixth aspect of the present invention.

Second Embodiment

Configuration of Air-Fuel Ratio Sensor

Figure 2:
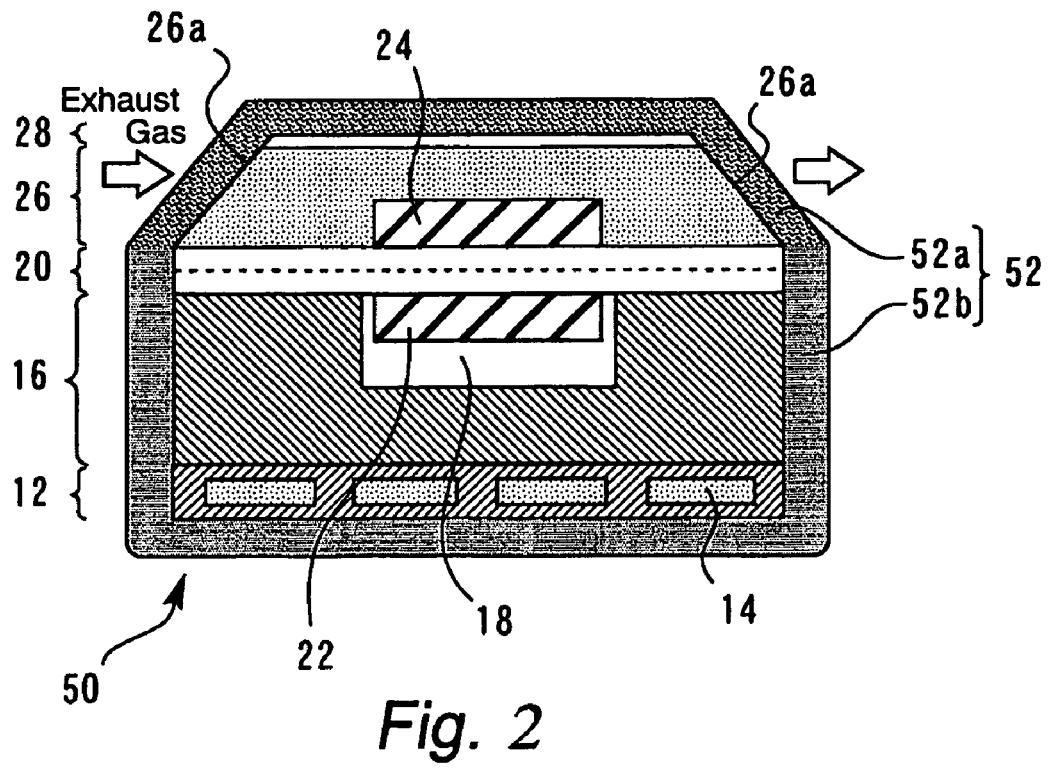
FIG. 2 is a diagram illustrating the configuration of a multilayered air-fuel ratio sensor 50 for use in a second embodiment of the present invention.

FIG. 2 is a diagram illustrating the configuration of a multilayered air-fuel ratio sensor 50 for use in a second embodiment of the present invention. The air-fuel ratio sensor 50 is similar in configuration to the air-fuel ratio sensor 10 shown in FIG. 1 except for a later-described trap layer 52.

As shown in FIG. 2, the air-fuel ratio sensor 50 according to the second embodiment includes a trap layer 52, which is positioned to cover the entire circumferential surface of a sensor element that is exposed to a space in the exhaust path. As is the case with the trap layer 30 shown in FIG. 1, the trap layer 52 is made of porous ceramics (alumina). Further, the porosity of the trap layer 52, which covers the sensor element, varies from one region to another. More specifically, a trap layer 52a made of a high-porosity material is positioned in a region that covers the vicinity of the inlet/outlet section 26a of the diffusion resistance layer 26 for the sensor element. In addition, another trap layer 52b, which is made of a material having a lower porosity than the above-mentioned trap layer 52a, is positioned in a region that mainly covers the heater layer 12 and the atmospheric layer formation layer 16. The trap layer 52a is equal in thickness to the trap layer 52b.

Features of Second Embodiment

Features of the second embodiment will now be described. In the air-fuel ratio sensor 10 according to the first embodiment, which has been described earlier, the thin trap layer 30a is positioned near the inlet/outlet section 28a of the diffusion resistance layer 26 to reduce the amounts of rich gas components that attach to the vicinity of the inlet/outlet section 28a during a period of engine inactivity.

On the other hand, the second embodiment is characterized in that the trap layer 52a positioned near the inlet/outlet section 28a of the diffusion resistance layer 26 has a high porosity. In other words, the amounts of rich gas components that attach to the trap layer 52 during a period of engine inactivity are small because the surface area decreases with an increase in the porosity of the trap layer 52. Therefore, the amounts of rich gas components that attach to the vicinity of the inlet/outlet section 28a during a period of engine inactivity can be effectively decreased by increasing the porosity of the trap layer 52a. This makes it possible to effectively avoid a situation where the desorbed rich gas components enter the diffusion resistance layer 26 during warm-up of the engine to increase the period during which sensor output deviation persists.

Further, the low-porosity trap layer 52b covers the vicinity of the heater layer 12 in which the sensor element is likely to crack. A decrease in trap layer porosity will reduce thermal shock that the sensor element undergoes due to water soaking. Therefore, a portion of the sensor element that is covered by the trap layer 52b is effectively protected from thermal shock caused by water soaking.

Furthermore, the high-porosity trap layer 52a covers the vicinity of the diffusion resistance layer 26 to provided enhanced functionality, as described earlier. Therefore, the present embodiment assumes that the trap layer 52a is equal in thickness to the trap layer 52b, that is, the trap layer 52a has a sufficient thickness to exhibit adequate water soak resistance. Consequently, a portion of the sensor element that is covered by the high-porosity trap layer 52a is also effectively protected from thermal shock caused by water soaking.

As described above, the air-fuel ratio sensor 50 according to the present embodiment uses the trap layers 52a, 52b, which differ in porosity, to effectively avoid a situation where sensor output deviation persists for a long period of time and effectively prevent the sensor element from being cracked by water soaking. This makes it possible to simultaneously enhance the air-fuel ratio sensor's functionality and water soak resistance.

The second embodiment, which has been described above, assumes that the air-fuel ratio sensor 50 includes the trap layers 52a, 52b, which differ in porosity, to simultaneously enhance the sensor's functionality and water soak resistance. However, the present invention is applicable not only to air-fuel ratio sensors but also to oxygen sensors and other exhaust gas sensors as far as they are multilayered and exposed to the gas to be measured.

Further, the second embodiment, which has been described above, assumes that the trap layer 52 is made of porous alumina. However, the present invention is not limited to the use of such a trap layer. More specifically, the trap layer 52 may be made of any porous ceramic materials.

Further, the second embodiment, which has been described above, assumes that the trap layer 52a is equal in thickness to the trap layer 52b. However, the thickness of the trap layer 52a need not always be equal to that of the trap layer 52b. More specifically, the trap layer 52a near the inlet/outlet section 28a of the diffusion resistance layer 26 may be thinner than the trap layer 52b, as is the case with the air-fuel ratio sensor 10 according to the first embodiment. This makes it possible to effectively shorten the period during which sensor output deviation persists in a warm-up process, thereby further enhancing the sensor's functionality.

In the second embodiment, which has been described above, the air-fuel ratio sensor 10 corresponds to the "exhaust gas sensor" according to the third aspect of the present invention; the trap layer 30a corresponds to the "first trap layer" according to the third aspect of the present invention; and the trap layer 30b corresponds to the "second trap layer" according to the third aspect of the present invention.

The invention claimed is:

1. An exhaust gas sensor that is multilayered and exposed to a space in an exhaust path of an internal combustion engine, the exhaust gas sensor comprising:
    an electrolyte layer which is positioned between an exhaust electrode and an atmosphere electrode to permit the movement of oxygen ions between the electrodes;
    an atmospheric layer formation layer which is placed on the atmosphere electrode side of the electrolyte layer to form an atmospheric layer to which the atmosphere electrode is exposed;
    a diffusion resistance layer which is porous and placed on the exhaust electrode side of the electrolyte layer to control the flow rate of an exhaust gas reaching the exhaust electrode;
    a shield layer placed on top of the diffusion resistance layer defining a gas inlet/outlet section of the diffusion resistance layer so that an inlet/outlet for the gas flowing into the diffusion resistance layer is limited to the gas inlet/outlet section of the diffusion resistance layer; and
    a trap layer which is porous and formed to cover portions of the sensor exposed to the space in the exhaust path;
    wherein the trap layer includes a first trap layer, which covers a region overlying the gas inlet/outlet section of the diffusion resistance layer, and a second trap layer, which covers a region that is not covered by the first trap layer and at least overlying the atmospheric layer formation layer, the first trap layer being thinner than the second trap layer.

2. The exhaust gas sensor according to claim 1, further comprising:
    a heater layer in which a heater is embedded to heat the electrolyte layer;
    wherein the second trap layer is formed to cover a region overlying the heater layer.

3. An exhaust gas sensor that is multilayered and exposed to a space in an exhaust path of an internal combustion engine, the exhaust gas sensor comprising:
    an electrolyte layer which is positioned between an exhaust electrode and an atmosphere electrode to permit the movement of oxygen ions between the electrodes;
    an atmospheric layer formation layer which is placed on the atmosphere electrode side of the electrolyte layer to form an atmospheric layer to which the atmosphere electrode is exposed;
    a diffusion resistance layer which is porous and placed on the exhaust electrode side of the electrolyte layer to control the flow rate of an exhaust gas reaching the exhaust electrode;
    a shield layer placed on top of the diffusion resistance layer defining an inlet/outlet section of the diffusion resistance layer so that an inlet/outlet for the gas flowing into the diffusion resistance layer is limited to the gas inlet/outlet section of the diffusion resistance layer; and
    a trap layer which is porous and formed to cover portions of the sensor exposed to the space in the exhaust path;
    wherein the trap layer includes a first trap layer, which covers a region overlying the gas inlet/outlet section of the diffusion resistance layer, and a second trap layer, which covers a region that is not covered by the first trap layer and at least overlying the atmospheric layer formation layer, the first trap layer being higher in porosity than the second trap layer.

4. The exhaust gas sensor according to claim 3, further comprising:
    a heater layer in which a heater is embedded to heat the electrolyte layer;
    wherein the second trap layer is formed to cover a region overlying the heater layer.

5. The exhaust gas sensor according to claim 3, wherein the first trap layer is equal in thickness to the second trap layer.

* * * * *